United States Patent [19]

Shinoda

[11] Patent Number: 5,631,942
[45] Date of Patent: May 20, 1997

[54] X-RAY DIAGNOSIS APPARATUS AND METHOD THEREOF

[75] Inventor: Katsuaki Shinoda, Tochigi-ken, Japan

[73] Assignee: Kabushiki Kaisha Toshiba, Kawasaki, Japan

[21] Appl. No.: 612,481

[22] Filed: Mar. 7, 1996

Related U.S. Application Data

[63] Continuation of Ser. No. 221,562, Apr. 1, 1994, abandoned.

[30] Foreign Application Priority Data

Apr. 1, 1993 [JP] Japan .................................. 5-075875

[51] Int. Cl.⁶ ........................................................ H05G 1/64
[52] U.S. Cl. .............................. 378/98.12; 378/98.2
[58] Field of Search .............................. 378/98.2, 98.12

[56] References Cited

U.S. PATENT DOCUMENTS

4,613,983  9/1986  Yedid et al. ........................ 378/98.2

*Primary Examiner*—Craig E. Church
*Attorney, Agent, or Firm*—Oblon, Spivak, McClelland, Maier & Neustadt, P.C.

[57] ABSTRACT

An X-ray diagnosis apparatus which divides a desired scope of diagnosis for a subject under examination from a first diagnosis position to a second diagnosis position into a plurality of diagnosis regions and produces an X-ray image of each of the diagnosis regions, thereby obtaining consecutive X-ray images covering the scope of diagnosis. The apparatus includes an input means for inputting at least a third diagnosis position within the scope of diagnosis and a setting means for setting the center-to-center distance of adjacent diagnosis regions on the basis of the distance between the first diagnosis position and the third diagnosis position.

18 Claims, 4 Drawing Sheets

X-RAY DIAGNOSIS APPARATUS AND METHOD THEREOF

This application is a continuation of application Ser. No. 08/221,562, filed on Apr. 1, 1994, now abandoned.

BACKGROUND OF THE INVENTION

1. Field of the Invention

The present invention relates to an X-ray diagnosis apparatus and a method thereof and, more particularly, to an X-ray diagnosis apparatus which examines by X-ray photography or fluoroscopy a plurality of regions of a subject under examination consecutively and a method thereof.

2. Description of the Related Art

One method of diagnosing diseases in circulatory organs is catheter examination. This catheter examination is made in an examination room in which an X-ray diagnosis apparatus and a bed for catheter examination (hereinafter referred to as a "catheter bed") are installed.

Figure 1:
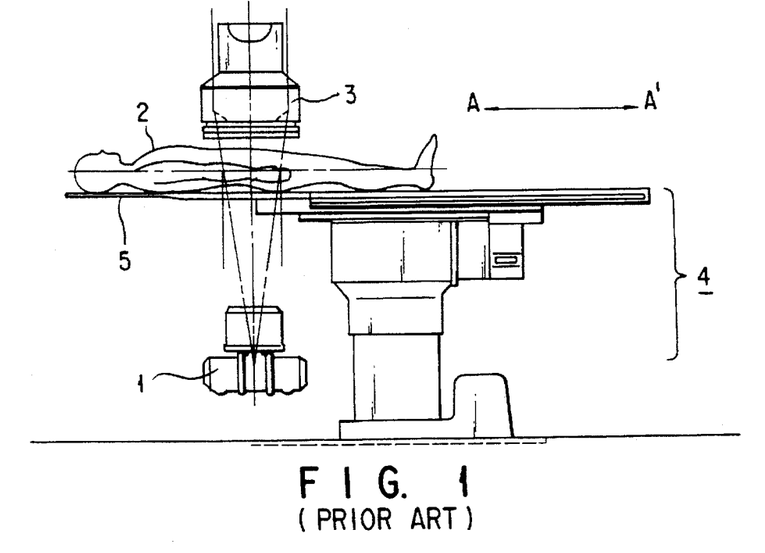
FIG. 1 is a schematic representation of a conventional X-ray diagnosis apparatus.

FIG. 1 is a schematic representation of the whole structure of a prior art X-ray diagnosis apparatus.

Under the control of an X-ray controller (not shown) an X-ray tube 1 irradiates x-rays onto a subject 2. The X-rays transmitted through the subject 2 are converted by an image intensifier 3 into an optical image, which, in turn, is entered through an optical system (not shown) into a TV camera (not shown) for conversion into a TV picture signal. The subject 2 is laid on a top board 5 placed on a catheter bed 4. The top board 5 is movable in both A and A' directions as shown in FIG. 1.

Using such an X-ray diagnosis apparatus as described above, a catheter examination of blood vessels in a leg is made as follows.

A catheter is inserted into a blood vessel and a blood vessel contrast medium is injected from the tip of the catheter into the blood vessel. The top board 5 of the catheter bed 4 on which the subject 2 is laid is moved in steps in the direction of A in FIG. 1 in synchronism with the speed with which the contrast medium progresses from the abdomen to the foot (hereinafter this movement is referred to as "leg stepping"). While the top board 5 is moved, examination by X-ray photography or fluoroscopy is made on the subject 2, using the X-ray tube 1 at regularly spaced intervals, i.e., for each of predetermined positions (or desired positions) of the leg of the subject (hereinafter referred to as "stage position"). This operation is hereinafter referred to as simply "stepping photography". This stepping photography permits visual observation of blood vessels in the entire leg, permitting an understanding of the conditions of diseases in circulatory organs of the subject.

With the leg stepping described above, it is required that a stenosis of a blood vessel of the subject 2 be located in the center of an X-ray image. That is, it is required to position the subject 2 by means of fluoroscopy prior to X-ray examination so that a desired portion of the subject 2 is placed in position, i.e., in the predetermined stage position. In almost every case, the stenosis will be produced at the place below the knee where three blood vessels branch off. The positioning is normally performed so that the place where blood vessels branch off is set in the fourth stage position. For the catheter bed 4 that is currently used, the number of movement steps is fixed at four and the number of stage positions is fixed at five. It is therefore difficult to position the subject 2 so as to entirely cover from an abdomen to an end of foot (hereinafter referred to as a "foot end"). If the foot tip cannot be covered, a method of photographing only the foot separately is adopted.

The leg stepping as described above will be described in more detail with reference to FIG. 2.

Figure 2:
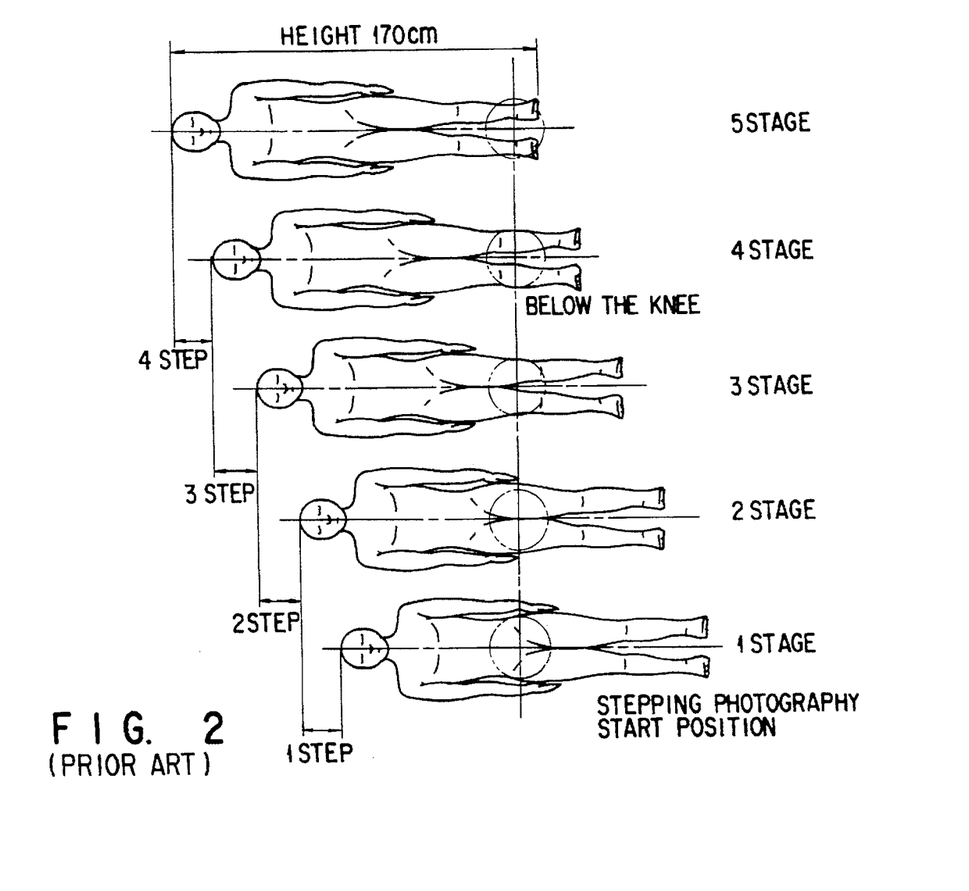
FIG. 2 is a diagram for use in explanation of stepping photography for leg stepping in the apparatus of FIG. 1.

FIG. 2 is a diagram for use in explanation of the stepping photography of leg stepping. In the conventional leg stepping, the stepping photography is sequentially performed at successive stages from the first stage (the stepping starting position) to the fifth stage, these stages being regularly spaced at a fixed interval (hereinafter referred to as "step size"). As described above, not only the step size but also the number of stages is fixed. If, therefore, in FIG. 2, the stepping photography is started at the first stage, the portion below the knee of the subject 2 will not necessarily be placed in the center of the photography area at the fourth stage because each subject to be examined has a different height. Since the leg length also varies from subject to subject, the entire leg will not necessarily fit within the scope of the stepping photography.

On the conventional catheter bed for leg stepping, the number of steps and the step size are fixed as described above. Therefore, in order to cover the desired photography scope fully, the stepping photography start position (e.g., the abdomen of a subject) is shifted backward and forward for position adjustment. In this case, in order to position a stenosed portion to be photographed, i.e., the place where three blood vessels branch off, in the fourth stage suitably, it is required to shift the top board 5 over and over again with X-ray fluoroscopy carried out for verification. For this reason, the subject 2 and an operator will be exposed to more X-rays than is necessary. Further, since the scope of stepping photography varies with the height of each subject to be examined, the positioning work is difficult and takes a lot of time.

In the above description, problems with leg stepping are described with respect to the case where the catheter bed 4 is shifted. The same can be said of the case where the X-ray tube is shifted for the stepping photography.

In the conventional X-ray diagnosis apparatus, as described above, since the number of steps and the step size for stepping photography are fixed, the positioning of a subject under examination has to be performed by shifting the top board 5 utilizing fluoroscopy for verification thereby to change the stepping photography start position so that the desired photography scope can be covered and a body portion to be examined can be placed in position. With this method, however, the positioning work is difficult because the scope of photography varies with the height of each subject to be examined.

SUMMARY OF THE INVENTION

It is an object of the present invention to provide an X-ray diagnosis apparatus and a method thereof which facilitate the positioning of a subject under examination in performing stepping photography.

According to an aspect of the present invention there is provided an X-ray diagnosis apparatus for dividing a desired scope of diagnosis for a subject under examination from a first diagnosis position to a second diagnosis position into a plurality of diagnosis regions and obtaining consecutive X-ray images of said diagnosis regions within said scope of diagnosis comprising: input means for inputting at least a third diagnosis position within said scope of diagnosis; and setting means for setting the distance between adjacent ones of said diagnosis regions on the basis of the distance between said first diagnosis position and said third diagnosis position.

The setting means is characterized by including means for setting said third diagnosis position in a fourth diagnosis region, by including means for setting the number of said diagnosis regions to one plus the number of diagnosis regions of as far as said third diagnosis position, by including means for setting the center-to-center distance of said diagnosis regions so that it is equal to or less than three-fourth of the diameter of said X-ray images and means for setting the number of said diagnosis regions including said first and second diagnosis positions according to the center-to-center distance of said diagnosis regions, or by including means for setting the number of said diagnosis regions to one plus the number of diagnosis regions of as far as said third diagnosis position.

Further, the X-ray diagnosis apparatus is characterized in that said input means includes means for inputting said second diagnosis position, and said setting means includes means for setting the number of said diagnosis regions so that said X-ray images cover said second diagnosis position.

According to the other aspect of the present invention there is provided an X-ray diagnosis method for dividing a desired scope of diagnosis for a subject under examination into a plurality of diagnosis regions and obtaining X-ray images of said diagnosis regions to thereby obtain consecutive X-ray images covering said scope of diagnosis, comprising: a first step of inputting at least one diagnosis position within said scope of diagnosis; and a second step of setting the center-to-center distance of adjacent diagnosis regions on the basis of the distance between a diagnosis start position and said diagnosis position set by said first step.

The X-ray diagnosis method is further characterized in that said first step includes a step of inputting a diagnosis termination position within said scope of diagnosis, and said second step includes a step of setting the number of said diagnosis regions so that said X-ray images cover said diagnosis termination position.

According to the present invention, a desired diagnosis position (stage position) within a scope of diagnosis need merely be input. When diagnosis is started from the diagnosis start position, a step size for stepping photography is automatically determined from the spacing between the diagnosis start position and the input diagnosis position. According to the present invention, therefore, the positioning of a subject under examination is permitted in a short period of time. This protects a subject under examination and an operator from excessive exposure to X-rays.

By inputting the final diagnosis position in addition to the desired diagnosis position, the number of steps can also be set, which facilitates the positioning of a subject under examination without being influenced by the height of the subject. Thus, the entire leg can be covered regardless of the subject's height, increasing the reliability of the X-ray diagnosis apparatus.

Additional objects and advantages of the present invention will be set forth in the description which follows, and in part will be obvious from the description, or may be learned by practice of the present invention. The objects and advantages of the present invention may be realized and obtained by means of the instrumentalities combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which.

DETAILED DESCRIPTION OF THE PREFERRED EMBODIMENT

An X-ray diagnosis apparatus and an X-ray diagnosing method of the present invention feature facilitation of the positioning of a subject under examination prior to examination (for example, leg DSA (digital subtraction angiography) stepping examination).

An X-ray diagnosis apparatus embodying the present invention will be described in detail with reference to the drawings.

Figure 3:
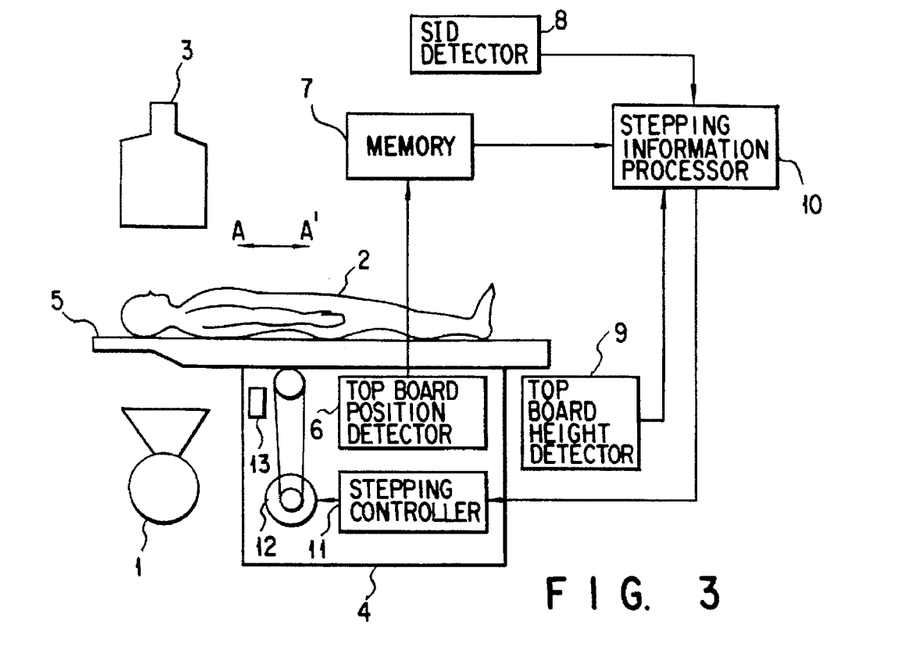
FIG. 3 is a schematic representation of an X-ray diagnosis apparatus embodying the present invention.

FIG. 3 is a schematic representation of an X-ray diagnosis apparatus according to an embodiment of the present invention.

The X-ray diagnosis apparatus of the present invention includes an X-ray tube 1, a top board 5, an image intensifier 3, a top board position detector 6, a memory device 7, an SID detector 8, a top board height detector 9, a stepping information processing unit 10, a stepping controller 11, a top board driver 12, and a memory switch 13.

The X-ray tube 1 irradiates X-rays onto a subject 2 under examination laid on the top board 5. The top board 5 is movable in both A and A' directions with the subject 2 laid thereon.

The image intensifier 3 detects X-rays transmitted through the subject 2 and converts them into an optical image.

The top board position detector 6 detects the position of the top board 5 in a direction of array A and A' and outputs a detected value.

The memory switch 13 is a switch for inputting such as a desired stage position and a final diagnosis position which will be described later in detail.

The memory device 7 records the position of the top board 5 detected by the top board height detector 6 corresponding to the input to the memory switch 13, stores the recorded data and outputs a stored result.

The SID detector 8 detects the distance between the focal point of the X-rays irradiated by the X-ray tube 1 and the image intensifier 3 and outputs a corresponding value.

The top board height detector 9 detects the height of the top board 5 and outputs a corresponding value.

The stepping information processing unit 10 is responsive to the outputs of the memory device 7, the SID detector 8 and the top board height detector 9 to automatically set the step size and the number of steps, which will be described later in detail.

The stepping controller 11 is responsive to the contents of processing by the stepping information processing unit 10 to perform stepping control of the top board 5.

The top board controller 12 is responsive to the stepping controller 11 to drive the top board 5.

The operation of the X-ray diagnosis apparatus thus arranged will be described.

Before proceeding with a description of the X-ray diagnosis apparatus of the present invention, it will serve us to give a brief outline of the leg DSA stepping examination.

The leg stepping is performed without injecting a blood vessel contrast medium into blood vessels of a subject under examination. That is, images of predetermined portions of the leg in the respective stage positions are taken by stepping photography prior to injection of the blood vessel contrast medium and then stored as mask images in a digital memory. Next, the blood vessel contrast medium is injected into a blood vessel of the subject. Then, the stepping photography is performed again in the same stage positions as at the time of collection of the mask images, thereby obtaining contrast images. A process of subtracting a contrast image collected in each stage position from a mask image in the corresponding stage position is performed successively thereby to obtain subtraction images from which image portions other than blood vessels are removed.

In particular, in the leg DSA stepping, the positioning of the subject under examination is performed prior to examination such that a stenosed portion is positioned in the center of an image. The place where the stenosed portion is produced normally corresponds to the place where three blood vessels branch off below the knee. Thus, the positioning is performed so that the place where three blood vessels branch off is basically set in the fourth stage position.

A reference will be made to FIG. 4 to describe a method to permit automatic positioning in accordance with the X-ray diagnosis apparatus of the present invention.

Figure 4:
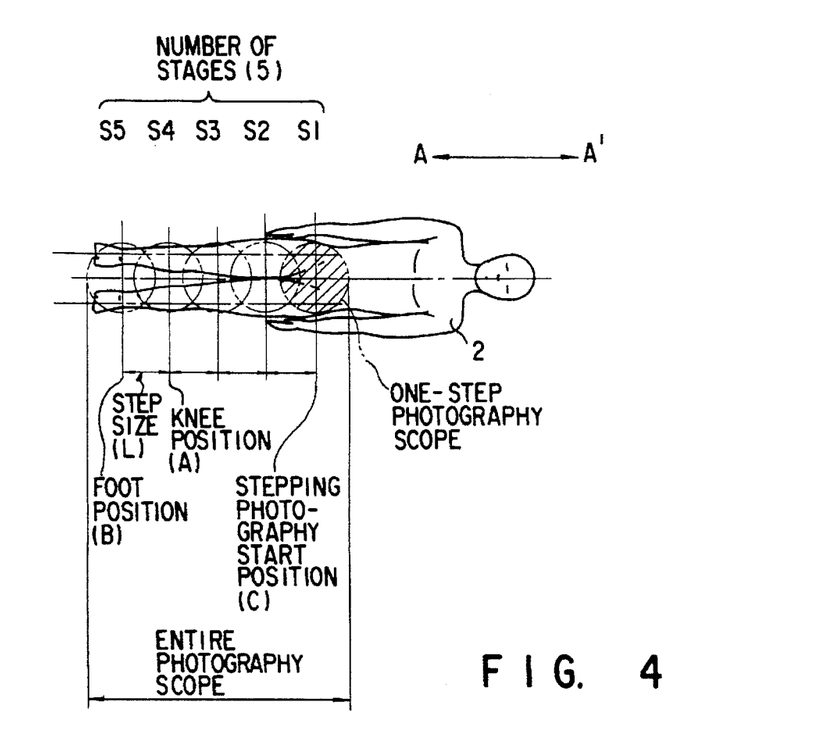
FIG. 4 is a diagram for use in explanation of a method of positioning a subject to be examined in accordance with the present invention.

In FIG. 4, each circle drawn by a broken line indicates a photography area of one step and a shaded circle indicates a photography area in the stepping photography starting position.

With X-ray fluoroscopy put into effect, the top board 5 (the subject 2), which has been set free, is shifted manually in the A and A' direction so that the place where three blood vessels branch off below the knee is positioned in the center of the radiation field of X-rays (the knee position at point A). This stage position is recorded in the memory device 7 by operation of the memory switch 13 as the fourth stage position (S4).

Subsequently, the top board 5 is further moved to the place (the foot end position at point B) where the foot end of the subject 2, i.e., the diagnosis termination position, is positioned in the center of the radiation field of X-rays. This position is recorded in the memory device 7 by operation of the memory switch 13 as the final diagnosis position. In the normal leg stepping, this final diagnosis position corresponds to the fifth stage position (S5).

Next, the top board 5 is shifted to the place where the stepping photography starting position (the abdomen at point C) comes to the center of the radiation field of X-rays. The position of the point C is recorded in the memory device 7 by operation of the memory switch 13 as the first stage position (S1).

A method of setting the number of steps and the step size by inputting the points A, B, and C will be described next.

The distance between the points A and C is divided equally into three parts. One-third of the distance between the points A and C is set as the step size L. In this case, the points C and A correspond to the first stage and the fourth stage, respectively, and the two intermediate points by which the distance between the points C and A is trisected are set as the second stage and the third stage, respectively.

In performing the stepping photography in succession in accordance with the step size thus set, the number of steps is set so that the fifth stage at the point B can be covered. If, in this case, the distance between the points A and B is equal to or less than the step size L, then all the desired diagnosis scope will be covered by the stepping photography of as far as the fifth stage. Thus, the number of steps is set at four and the number of stages is set at five. If, on the other hand, the distance between the points A and B is greater than the step size L, then all the desired diagnosis scope will not be covered so long as the number of steps is four. In this case, the number of steps is set to 5 or more so that a further stage is set beyond the point B.

When an operator inputs information on the three points A, B and C as described above, the number of steps and the step size for stepping photography are set automatically. This facilitates positioning of a subject 2 in stepping photography.

Figure 5:
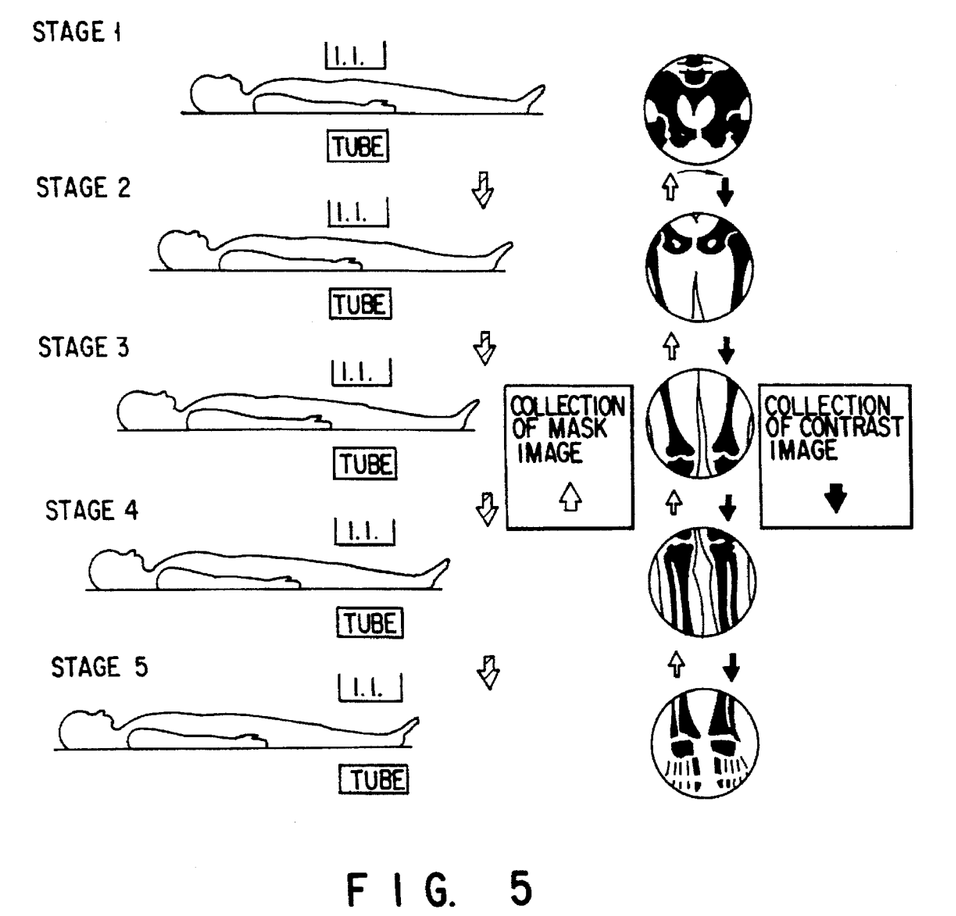
FIG. 5 is a diagram for an operational procedure of the leg DSA stepping.

An operational procedure for the leg DSA stepping will be described with reference to FIG. 5 more specifically.

(1) The respective positions of the top board 5 when a portion below the knee and the foot of a subject under examination laid on the top board are each placed in the center of the radiation area of X-rays are entered into the memory device 7 by operation of the memory switch 13. In the following description, as in the above, suppose that the position of the top board 5 when the knee is placed in the photography center corresponds to the point A (STAGE 4) and the position of the top board when the foot is covered by the photography area corresponds to the point B (e.g., STAGE 5).

(2) The top board 5 is shifted to the stepping start position (supposed to be the point C; Stage 1), which is the abdomen of the subject, so that it is enabled for stepping operation. At this time, the start position (point C) is entered into the memory device 7 by the memory switch 13. By recording the start position (point C), the number of steps and the step size are automatically set by the stepping information processing unit 10, so that the position of each stage for stepping photography is also obtained.

In this case, an input order of each point of points A, B and C is not limited to the above input order, each point can be input in a desired order. The memory device 7 stores the data input by the memory switch 13 in accordance with the magnitude thereof and sets the data to the corresponding points A, B and C.

(3) While the subject under examination is being subjected to fluoroscopy, the top board 5 is moved from start position (STAGE 1) in steps in the direction of the foot end of the subject in accordance with the number of steps and the step size which have been set automatically (STAGE 1 to STAGE 5). While the top board 5 is moved, the following operation is performed. The X-ray conditions, e.g., X-ray tube voltage, positioning of aperture (for preventing halation) or the like, in each stage are set. A collection of the mask image and contrast image described later is performed based on the conditions set in this step.

The top board 5 is moved to the final stage. The position of the top board at the final stage serves as the mask image collection start position (STAGE 5).

(4) The top board 5 is moved in steps from the final stage, at which the collection of mask images is started, toward the first stage (i.e., in the direction from foot to head; in the direction of STAGE 5 to STAGE 1) while a fluoroscopic image is collected at each stage. The fluoroscopic images collected during this stepping operation of the top board 5 are used as mask images. The collection of mask images is performed until the top board 5 arrives at the first stage (the stepping operation start position; the point C). The position of the top board 5 at the first stage is made to be the contrast image collection start position.

(5) On termination of the mask image collection after the top board 5 has returned to the first stage, a blood vessel contrast medium is injected.

(6) The top board 5 is moved in steps from the first stage (the stepping operation start position; the point C) toward the final stage to acquire a fluoroscopic image at each stage while the flow of the blood vessel contrast medium is being traced (STAGE 1 to STAGE 5). The fluoroscopic images collected during the stepping operation of the top board serve as contrast images. The collection of the contrast images is performed until the top board arrives at the final stage (STAGE 5).

Thus, the sequence of operations (1) to (6) is terminated. Subsequently the normal DSA method is carried out to obtain subtraction images of the subject 2.

A method of setting the stage positions will be described specifically with reference to FIGS. 6A to 6E.

First, the diameter of the fluoroscopic images of the subject under examination is obtained from the distance (SID) between the focal point of the X-ray tube 1 and the image intensifier 3 and the height of the top board 5. A decision is then made on the basis of the diameter of the fluoroscopic images to what extent the fluoroscopic images at adjacent stages overlap each other. When the width of the overlap between the fluoroscopic images is equal to or more than a quarter of their diameter, the stepping information processing unit 10 decides that the overlap is adequate. When the width of the overlap is less than the diameter, on the other hand, the stepping processing unit decides that the overlap is inadequate.

Figure 6A:
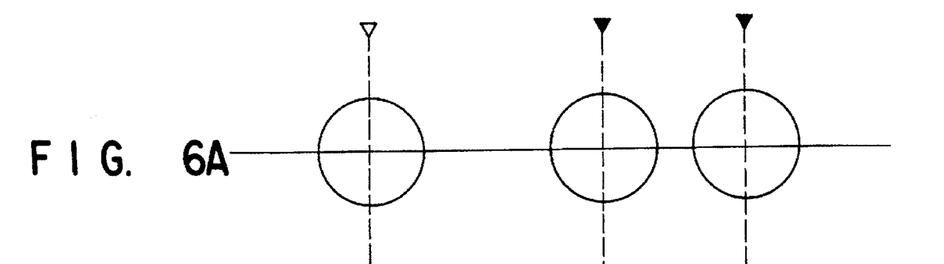
FIGS. 6A to 6E show a specific method of setting stage positions in accordance with the present embodiment.

(1) The position of the top board 5 at each of the points A and B is recorded on the memory device 7 by the memory switch 13 (FIG. 6A).

(2) The stepping operation start position (the point C) of the top board 5 is entered (FIG. 6A). The memory device 7 stores the input points A to C.

Figure 6B:
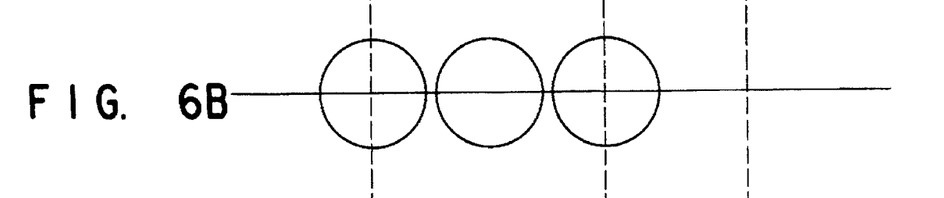

(3) The stepping information processing unit 10 divides the distance between the points C and A equally into two (FIG. 6B). In this case, the fluoroscopic images do not overlap each other at all and thus the stepping information processing unit 10 will decide that the overlap is not adequate.

Figure 6C:
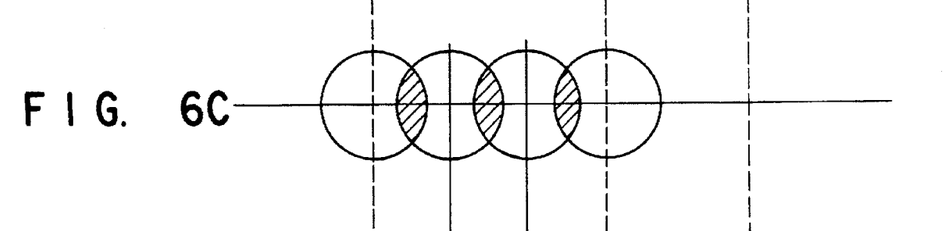

(4) The stepping information processing unit 10 divides the distance between the points C and A equally into three (FIG. 6C). In this case, the width of overlap between fluoroscopic images is equal to or greater than one-fourth of their diameter. The stepping information processing unit 10 thus decides that the overlap is adequate and then sets intermediate stages with the step size by which the distance between the points C and A is divided equally into three. The area where the fluoroscopic images overlap each other is indicated shaded.

Figure 6D:
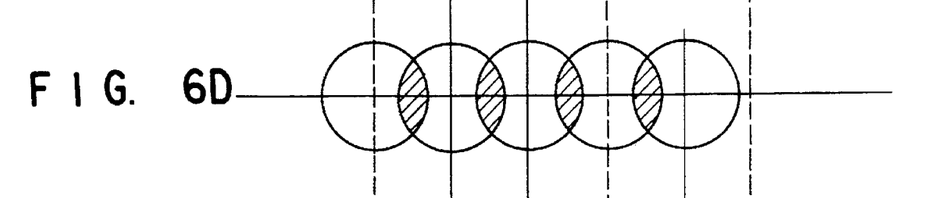

(5) When the point B is not entered (that is, when the feet of the subject need not be covered), a further stage is set at the B point side of the fourth stage (the point A) with the step size determined by the stepping information processing unit 10. That is, the number of steps and the step size are set by the stepping information processing unit 10 so that the 5-stage operation is performed (FIG. 6D).

Figure 6E:
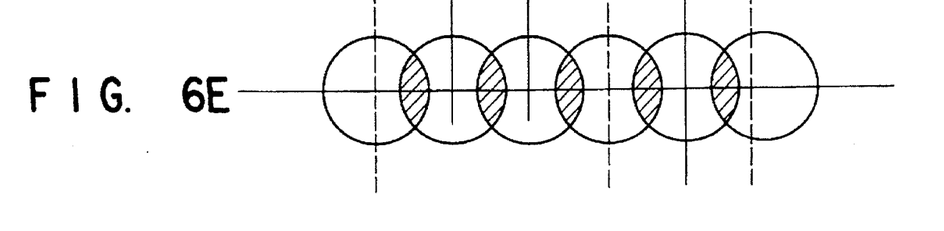

(6) When the point B is entered, a decision is made as to how many stages are further required in order to cover as far as the point B with the step size set by the stepping information processing unit 10. In this case, the number of steps and the step size are set by the stepping information processing unit 10 so that two stages are further set up and hence a 6-stage operation is performed (FIG. 6E).

According to the present invention, as described above, an operator simply enters three points of A, B, and C. In response to this, the stepping information processing unit 10 automatically sets the number of steps and the step size needed for the stepping photography. This facilitates the positioning of a subject under examination for the stepping photography.

The present invention is not restricted to the above embodiment.

In the above embodiment, an example of entering three points of A, B, and C and an example of entering two points of A and C were described with respect to the positioning for covering as far as the feet of a subject under examination. The point C, which is the stepping photography start position, need also not be entered if the leg stepping need not be repeated on the same conditions. The point C may be entered at the same time the stepping photography is started.

In the above example, the number of steps and the step size are automatically set to shift the top board of the catheter bed for leg stepping. Instead of shifting the top board, the X-ray tube may be shifted in steps. In this case, of course, the present invention can also be applied to set the number of steps and the step size for the movement of the X-ray tube. That is, the present invention is adaptable to any X-ray photography which is performed in steps.

In the above embodiment, the number of divisions of the distance between the points A and C is increased, such as two, three, etc., according to the overlap between fluoroscopic images. If the overlap between fluoroscopic images is inadequate, then the distance between the points C and A may be further divided with the point A basically used as the fourth stage position. In this case, the point A will be a stage following the fifth stage. An operator may enter the stage number for the point A together with the point A. The number of steps may be entered by the operator like the stage number.

It goes without saying that the present invention may be practiced or embodied in still other ways without departing from the scope thereof.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An X-ray diagnosis apparatus for obtaining plural contiguous X-ray images covering a desired scope of diagnosis for a subject under examination from a first diagnosis position to a second diagnosis position, comprising:

input means for inputting said first and second diagnosis positions and a third diagnosis position within said scope of diagnosis;

X-ray generating means for irradiating said subject with X-rays having a predetermined radiation pattern;

imaging means for obtaining an image of X-rays irradiated by said X-ray generating means and passing through the subject;

setting means for setting a center-to-center spacing between adjacent X-ray images on the basis of the distance between said first diagnosis position and said third diagnosis position and a size of said predetermined radiation pattern so that plural contiguous X-ray images can be obtained between said first and second diagnosis positions, with one of the contiguous X-ray images centered on said third diagnosis position; and control means for controlling said X-ray generating means and said imaging means to obtain said plural contiguous X-ray images from said first diagnosis position to said second diagnosis position, including said one of the X-ray images centered on said third diagnosis position, at the spacing set by said setting means.

2. The X-ray diagnosis apparatus according to claim 1, wherein said setting means includes means for setting said center-to-center spacing and the number of said contiguous X-ray images so that said contiguous X-ray images cover said second diagnosis position.

3. The X-ray diagnosis apparatus according to claim 1, wherein said setting means includes means for setting said center-to-center spacing and the number of said contiguous X-ray images such that said third diagnosis position is centered in a fourth of said contiguous X-ray images counted from one of said first and second positions.

4. The X-ray diagnosis apparatus according to claim 3, wherein said setting means includes means for setting the center-to-center spacing and the number of said contiguous X-ray images so that said contiguous X-ray images cover said second diagnosis position.

5. The X-ray diagnosis apparatus according to claim 3, wherein said setting means includes means for setting the center-to-center spacing and the number of said contiguous X-ray images such that the number of said of said contiguous X-ray images is one plus the number of contiguous X-ray images extendinq from one of said first and second diagnosis positions and covering said third diagnosis position.

6. The X-ray diagnosis apparatus according to claim 1, wherein said setting means includes:

means for setting the center-to-center spacing so that said center-to-center spacing is equal to or less than ¾ of the diameter of one of said contiguous X-ray images, and means for setting the number of said contiguous X-ray images to cover said first and second diagnosis positions.

7. The X-ray diagnosis apparatus according to claim 6, wherein said setting means includes means for setting the center-to-center spacing of the contiguous X-ray images and the number of said contiguous X-ray images so that said contiguous X-ray images cover said second diagnosis position.

8. The X-ray diagnosis apparatus according to claim 6, wherein said setting means includes means for setting the enter-to-center spacing and the number of said contiguous X-ray images such that the number of said contiguous X-ray images is equal to one plus the number of contiguous X-ray images extending from one of said first and second diagnosis positions and covering said third diagnosis position.

9. The X-ray diagnosis apparatus according to claim 1, comprising:

a subject support; and sensing means for sensing a present position of said subject support.

10. The X-ray diagnosis apparatus according to claim 9, wherein said setting means includes:

means for setting said center-to-center spacing so that said center-to-center spacing is equal to or less than ¾ of the diameter of one of said contiguous X-ray images, and means for setting the number of said contiguous X-ray images to cover said first and second diagnosis positions.

11. The X-ray diagnosis apparatus according to claim 10, wherein said setting means includes means for setting said center-to-center spacing and the number of said contiguous images such that the number of said contiguous X-ray images is equal to one plus the number of contiguous X-ray images extendinq from one of said first and second diagnosis positions and covering said third diagnosis position.

12. The X-ray diagnosis apparatus according to claim 9, wherein said input means includes means for inputting said third diagnosis position based on the position sensed by said sensing means when the support is positioned with respect to said X-ray generating means such that X-rays from said X-ray generating means irradiate said third diagnosis position.

13. The X-ray diagnosis apparatus according to claim 9, wherein said setting means includes means for setting said center-to-center spacing and the number of said contiguous X-ray images so that said contiguous X-ray images cover said second diagnosis position.

14. The X-ray diagnosis apparatus according to claim 9, wherein said setting means includes means for setting said center-to-center spacing and the number of said contiguous images such that said third diagnosis position is centered in a fourth of said contiguous X-ray images counted from one of said first and second positions.

15. The X-ray diagnosis apparatus according to claim 14, wherein said setting means includes means for setting said center-to-center spacing of said contiguous images and the number of said contiguous X-ray images so that said contiguous X-ray images cover said second diagnosis position.

16. The X-ray diagnosis apparatus according to claim 14, wherein said setting means includes means for setting said center-to-center spacing and the number of said contiguous X-ray images such that the number of said contiguous X-ray images is one plus the number of of contiguous X-ray images extending from one of said first and second positions and covering said third diagnosis position.

17. The X-ray diagnosis apparatus according to claim 10, wherein said setting means includes means for setting said center-to-center spacing and the number of said contiguous X-ray images so that said contiguous X-ray images cover said second diagnosis position.

18. An X-ray diagnosis apparatus for obtaining plural contiguous X-ray images a desired scope of diagnosis for a subject under examination, comprising:

input means for inputting a start position and a position of interest within said scope of diagnosis;

X-ray generating means for irradiating said subject with X-rays having a predetermined radiation pattern;

setting means for setting a center-to-center spacing between adjacent X-ray images on the basis of said first position and the position of interest input by the input means and a size of said predetermined radiation pattern so that plural contiguous X-ray images can be obtained, said plural contiguous X-ray images extending from said first position past said position of interest to an end position which is the center-to-center spacing away from said position of interest, with one of the contiguous X-ray images centered on said position of interest; and control means for controlling said X-ray generating means and said imaging means to obtain said plural contiguous X-ray images from said first position to the end position, including said one of the X-ray images centered on said position of interest, at the spacing set by said setting means.

* * * * *